US006338834B1

(12) United States Patent
Jurisson et al.

(10) Patent No.: US 6,338,834 B1
(45) Date of Patent: Jan. 15, 2002

(54) MELANOTROPIN ANALOGS FOR POTENTIAL RADIOPHARMACEUTICALS FOR DIAGNOSIS AND TREATMENT OF MELANOMA

(75) Inventors: Silvia S. Jurisson; Thomas P. Quinn, both of Columbia, MO (US); Michael F. Giblin, Long Beach, CA (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 09/070,276

(22) Filed: Apr. 30, 1998

(51) Int. Cl.[7] .................... A61K 51/00; A61M 36/14
(52) U.S. Cl. ................ 424/1.69; 424/1.11; 424/1.65; 424/9.1; 534/14; 534/7; 530/300; 530/312; 530/317
(58) Field of Search ................ 424/1.11, 1.65, 424/1.69, 9.1; 530/300, 317, 326, 327, 312; 514/11; 534/7, 10–16

(56) References Cited

U.S. PATENT DOCUMENTS

| | | |
|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,925,678 A | 5/1990 | Ranney |
| 4,959,217 A | 9/1990 | Sanders et al. |
| 5,167,616 A | 12/1992 | Haak et al. |
| 5,169,383 A | 12/1992 | Gyory et al. |
| 5,225,182 A | 7/1993 | Sharma |
| 5,455,044 A | 10/1995 | Kim et al. |
| 5,558,852 A | 9/1996 | Bigner et al. |

OTHER PUBLICATIONS

Baidoo etal, Bioconjugate Chem. vol. 5, pp. 114–118, Bifunctional Chelator for Facile Preparation of Néutral Technetium Complexes, 1994.*

Al–Obeidi, F., et al., Potent and Prolonged Acting Cyclic Lactam Analogues of α–Melanotropin: Design Based on Molecular Dynamics. (1989) *J. Med. Chem.*, 32, 2555–2561.

Hruby, et al., Design, Synthesis, and Conformation of Superpotent and Prolonged Acting Melanotropins. (1993) *Annals of the New York Acad. of Sci.*, 680, 51–63. (This Was Originally Cited Under the Name of Obidi, Incorrectly).

Bagutti, C., et al., [$^{111}$In]–DTPA–Labeled Analogues of α–Melanocyte–Stimulating Hormone For Melanoma Targeting: Receptor Binding In Vitro and In Vivo. (1994) *Int. J. Cancer*, 58, 749–755.

Bakker, W. H., et al.[$^{111}$IN–DTPA–D–PHE$^1$]–Octreotide, A Potential Radiopharmaceutical For Imaging Of Somatostatin Receptor–Positive Tumors: Synthesis, Radiolabeling and In Vitro Validation. (1991) *Life Sci.* 49, 1583–1591.

Bard, D.R., et al., A chelating derivative of α–melanocyte stimulating hormone as a potential imaging agent for malignant melanoma. (1990) *Br. J. Cancer*, 62, 919–922.

Betz, et al., 1994, Basic Neurochem. Molecular Cell, (Raven Press Ltd, NY) 5$^{th}$ Ed., 681–699.

Bickel, Ulrich, et al., Pharmacologic effects in vivo in brain by vector–mediated peptide drug delivery. (Apr. 1993) *Proc. Natl. Acad. Sci. USA*, 90, 2618–2622.

Brem, et al., Polymers as controlled drug delivery devised for the treatment of malignant brain tumors, (1993) *Eur. J. Pharm. Biopharm*, 39 2–7.

Bryan, Jeffrey C., et al, Oxygen Atom Transfer between Rhenium, Sulfur, and Phosphorus. Characterization and Reactivity of Re(O)Cl$_3$(Me$_2$S)(OPPh$_3$) and Re(O)Cl$_3$(CNCMe$_3$)$_2$. (1987) *Inorg. Chem.* 26, 2283–2288.

Chi, Dae Yoon, et al., Homodimeric and Heterodimeric Bis (amino thiol) Oxometal Complexes with Rhenium (V) and Technetium (V). Control of Heterodimeric Complex Formation and an Approach to Metal Complexes that Mimic Steriod Hormones. (1994) *J. Med. Chem.*, 37, 928–937.

Cody, Wayne L., et al., Cyclic Melanotropins. 9.$^1$ 7–D–Phenylalanine Analogues of the Active –Site Sequence. (1985) *J. Med. Chem.* 28, 583–588.

Ellman, George L., Tissue Sulfhydryl Groups. (1959) *Archives of Biochemistry and Biophysics*, 82, 70–77.

Franco, et al., Characterization of the Iron–binding Site in Mammalian Ferrochelatase by Kinetic and Mossbauer Methods, (1995) *Journ. Bio. Chem.* 270:44, 26352–26357.

Fritzberg, A.R., et al., Specific and stable labeling of antibodies with technetium–99m with a diamide dithiolate chelating agent (1988) *Proc. Natl. Acad. Sci U.S.A.*, 85, 4025–4029.

Garg, Pradeep K., et al., Enhanced Binding and Inertness to Dehalogenation of αMelanotropic Peptides Labeled Using N–Succinimidyl 3–Iodobenzoate, (1966) *Bioconjugate Chem.* 7, 233–239.

Giblin, Michael F., et al., Synthesis and Characterization of Rhenium–Complexed α–Melanotropin Analogs, (1997) *Bioconjugate Chem.*, 8, 347–353.

(List continued on next page.)

Primary Examiner—Dameron L. Jones
(74) Attorney, Agent, or Firm—Kohn & Associates

(57) ABSTRACT

A compound for use as a diagnostic or therapeutic pharmaceutical and method of using the same where the compound consists essentially of an alpha-melanotropin stimulating hormone analog which has integrally located a radionuclide. The radionuclide is administered to the body in an amount sufficient to allow uptake and retention by the tumor cells.

2 Claims, 3 Drawing Sheets

(1 of 3 Drawing Sheet(s) Filed in Color)

OTHER PUBLICATIONS

Grove, D.E., et al., Oxo–complexes of Rhenium(v) (1966) *J. Chem. Soc. A* 1224–1230.

Grummon, Glenn, et al., Synthesis, Characterization and Crystal Structures of Technetium(V)–Oxo Complexes Useful in Nuclear Medicine. 1. Complexes of Mercaptoacetylglycylglycyglycine ($MAG_3$) and Its Methyl Ester Derivative ($MAG_3OMe$), (1995) *Inorg. Chem.* 34, 1764–1772.

Hansen, Lory, et al., Rhenium (V) Oxo Complexes Relevant to Technetium Renal Imaging Agents Derived from Mercaptoacetylglycylglycylaminobenzoic Acid Isomers. Structural and Molecular Mechanics Studies. (1992) *Inorg. Chem.* 31, 2801–2808.

Iverson, Brent L., et al., Metalloantibodies. *Science*, 249, 659–662.

Kellis, J.T. Jr., et al., Protein Stabilization By Engineered Metal Chelation (1991) *BioTechnology* 9, 994–995.

Klemba, Michael, et al., Novel metal–binding proteins by design. (1995) *Structural Biology*, 2:5, 368–373.

Krenning, E.P., et al., Somatostatin Receptor Scintigraphy with Indium–111–DTPA–D–Phe–1–Octreotide in Man: Metabolism, Dosimetry and Comparison with Iodine–123–Tyr–3–Octreotide. (May 1992) *Journ. Nuc. Med.* 33:5, 652–658.

Kruck, Theo P.a., et al., Molecular design to mimic the copper(II) transport site of human albumin: studies of equilibria between copper(II) and glycylglycyl–L–histidine–N–methyl amide and comparison with human albumin. (1976) *Can.J. Chem.* 54, 1300–1308.

Lau, et al., Synthesis and copper (II)–binding properties of the N–terminal peptide of human α–fetoprotein. (1989), 257, 745–750. *J. Biochem.*

Lever, Susan Z., et al., Inorganica Chimica Acta Letter, *Inorg. Chim. Acta*, (1996) 176, 183–184.

Liu, Shuang, et al., Labeling a Hydrazino Nicotinamide–Modified Cyclic IIb/IIIa Receptor Antagonist with $^{99m}Tc$ Using Aminocarboxylates as Coligands. (1996) *Bioconjugate Chem.* 7, 63–71.

Pardridge, William M., Recent Developments in Peptide Drug Delivery to the Brain. (1992) *Pharmacology & Toxicology*, 71, 3–10.

Pardridge, William M., et al., Blood–Brain Barrier and New Approaches to Brain Drug Delivery. (1992) *West J Med*, 156, 281–286.

Piotto, M., et al., Gradient–tailoed excitation for single–quantum NMR spectroscopy of aqueous solutions. (1992), *J. Biomol.*, NMR 2, 661–665.

Powell, M.J.D., Restart Procedures For the Conjugate Gradient Method (1977), *Mathematical Programming*, 12, 241–254.

Rao, T.N., et al., Technetium (V) and Rhenium(V) Complexes of 2,3–Bis (mercaptoacetamido)propanoate. Chelate Ring Sterochemistry and Influence on Chemical and Biological Properties. (1990) *J. Am. Chem. Soc.* 112, 5798–5804.

Regan, L., The Design Of Metal–Binding Sites in Protein (1993) *A. Rev. Biophys. Biomol. Struct.* 22, 257–281.

Sahm, Ulrike G., et al., Influence of α–MSH Terminal Amino Acids on Binding Affinity and Biological Activity in Melanoma Cells. (1994), Peptides, 15:3, 441–446.

Sambhi, Sharan K., et al., Local production of tumor necrosis factor encoded by recombinant vaccinia virus is effective in controlling viral replication in vivo. (May 1991) *Proc. Natl. Acad. Sci USA*, 88, 4025–4029.

Sawyer, Tomi K., et al., 4–Norleucine, 7–D–phenylalanine–α–melanotropin with ultralong biological activity. (Oct. 1980) *Proc. Natl. Acad. Sci. USA*, 77:10, 5754–5758.

Schöeth, Helgi B., et al., Selectivity of Cyclic [D–Nal$^7$] and [D–Phe$^7$] Substituted MSH Analogues for the Melanocortin Receptor Subtypes. (1997) *Peptides*, 18:7, 1009–1013.

Siegrest, W., et al., Characterization of Receptors for α–Melanocyte–stimulating Hormone on Human Melanoma Cells. (1989) *Cancer Research* 49, 6352–6358.

Siegrest, W., et al., Radioreceptor Assay For α–MSH Using Mouse B16 Melanoma Cells. (1988) *Journ. of Receptor Research*, 8, 323–343.

Siegrest, W., et al., In Situ Melanin Assay for MSH Using Mouse B16 Malanoma Cells in Culture. (1986) *Anal. Biochem.*, 159, 191–197.

Tatro, Jeffrey B., et al., Melanotropin Receptors of Murine Melanoma Characterized in cultured Cells and Demonstrated in Experimental Tumors in Situ. (Feb. 15, 1990) *Cancer Research*, 50, 1237–1242.

Vaidyanathan, G., et al., Fluorine–18–Labeled [Nle$^4$, D–Phe$^7$]–α–MSH, an αMelanocyte Stimulating Hormone Analogue. (1997) *Nuclear Med. & Biol.*, 24, 171–178.

Varnum, James M., et al., Stability and Conformational Analysis of Tc–RC160 and Re–RC160: Experimental and Theoretical Analysis of the Influence of Metal Complexation on the Structural Requisites for Activity. (1996) *J. Phys. Chem.*, 100, 14630–14636.

Varnum, James M., et al., Rhenium–labeled Somatostatin Analog RC–160. (1994) *Journ. Bio. Chem.*, 269:17, 12583–12588.

Wraight, E.P., et al., The use of a chelating derivative of alpha melanocyte stimulating hormone for the clinical imaging of malignant melanoma. (1992) *The British Journal of Radiology*, 65, 112–118.

\* cited by examiner

MELANOTROPIN ANALOGS FOR POTENTIAL RADIOPHARMACEUTICALS FOR DIAGNOSIS AND TREATMENT OF MELANOMA

BACKGROUND OF THE INVENTION

Metal ions often play critical roles in protein structure and function. Engineered metal-binding sites in peptides and proteins have been widely used to enhance structural integrity, stabilize biologically active conformations, and confer novel enzymatic activities (Iverson, B. L., 1990; Regan, L., 1993; Kellis, J. T. Jr., 1991). Biochemical and structural analyses of transition metal coordination by proteins and peptides have traditionally focused on zinc, copper, manganese, and iron due to their roles in important biological processes (Klemba, M., 1995; Kruck, T. P. A., 1976; Lau, S., 1989; Franco, R., 1995). Other transition metals, not found in natural proteins, have coordination, isotopic, and chemical properties which make them attractive for peptide and protein engineering. Rhenium (Re) and Technetium (Tc) are group VIIB transition metals which share similar coordination geometries and form stable complexes with amine and amide nitrogens, carboxylate oxygens, and thiolate and thioether sulfurs, with a strong preference for thiolate sulfurs (Vanbilloen, H. P., 1995). Radioactive isotopes of Re and Tc have significant medical applications due to the nature of their associated radiation and physical half-life properties.

The synthesis and characterization of radiolabeled antibodies, peptides, and steroid hormones as in vivo tumor imaging and therapeutic agents are active areas of cancer research today. These molecules specifically target tumor cells by virtue of their high specificities for receptors and antigens present on the surfaces of these cells. In one commonly used approach, metallic radionuclides such as $^{186}$Re, $^{188}$Re, and $^{99m}$Tc are appended to the tumor targeting molecule through bifunctional chelate groups which consist of a metal chelate and an activatable crosslinker (Bakker, W. H., 1991; Fritzberg, A. R., 1988; Liu, S., 1996). The resulting radiolabeled proteins, peptides, and small molecules are decorated with one or more chelating groups. The presence of bulky metal chelating groups and their associated crosslinkers may affect receptor affinity and biodistribution in vivo (Krenning, E. P., 1992; Wraight, E. P., 1992).

An alternative approach to the design of radiolabeled tumor imaging and therapeutic agents involves incorporating the metal directly into the molecule's structure (Varnum, J. M., 1994; Varnum, J. M., 1996; Chi, D. Y., 1994). Metal centers with defined coordination geometries can provide a foundation for the construction of stable molecular structures which have high affinities for specific receptors or antigenic sites. Protein, peptide, and small molecule structures can be designed to use metal coordination to reduce conformational freedom, stabilize active conformations, or mimic native conformations.

Alpha melanocyte stimulating hormone (α-MSH) is a tridecapeptide [Ac-Ser-Tyr-Ser-Met-Glu-His-Phe-Arg-Trp-Gly-Lys-Pro-Val-NH$_2$] that regulates skin pigmentation in most vertebrates (Hruby, V. J., 1993). The core α-MSH sequence His-Phe-Arg-Trp, conserved in a number of species, has been found to be sufficient for receptor recognition (Hruby, V. J., 1993). α-melanotropin is a naturally occurring tridecapeptide that specifically recognizes melanotropin receptors. Since mouse melanoma cells and human melanocytes possess α-melanotropin (α-MSH) receptors, the use of radiolabeled α-MSH analogs for diagnosis and treatment of α-MSH positive cancers (i.e., melanoma) was hypothesized. Various synthetic α-melanotropin analogs have been prepared and characterized for α-melanotropin activity by V. J. Hruby, M. E. Hadley et al. They have reported that cyclic analogs of α-MSH (as described by U.S. Pat. No. 4,485,039; 1984) display properties which increase their potency toward the α-MSH receptor, prolong their activity and increase their resistance to in vivo enzymatic degradation.

In 1990, D. R. Bard, C. G. Knight and D. P. Page-Thomas filed an international patent application for targeting malignant melanoma with multiple α-MSH analogs chemically attached to a chelating molecule (e.g. DTPA) which can subsequently be linked to a cytotoxic agent or radionuclide (e.g., In-111 or I-131). The literature reports by these authors describe the use of In-111-labeled analogs of the patented moieties for use as diagnostic agents for malignant melanoma.

The peptide analog used as the starting material for the Re and Tc labeling reactions was first described by Wayne L. Cody et al. as a superpotent α-MSH analog with prolonged biological activity. This analog is now commercially available. However, neither the use of Re or Tc to covalently cyclize α-MSH analogs, nor Re or Tc radiolabeling studies using this analog have been reported.

One radiolabeled α-MSH analog has been reported as a targeting agent of the radionuclide Indium-111. This analog consists of two des-acetyl-MSH molecules crosslinked through the chelating group DPTA. In vivo work on this analog was carried out under Home Office project license number PPL 70/00499, and was reported in Bard, D. R. et al. No studies have been reported which attach medically important radionuclides to α-MSH via peptide chelating groups.

The development of new diagnostic and therapeutic agents for treating cancer is an important area of research, since so many people develop cancer during their lifetimes. Melanomas are particularly difficult to treat successfully because they are very aggressive (early metastasis) and have proven resistant to general chemotherapy and external radiation treatment. The use of specific biological molecules, such as α-MSH, to target melanoma with diagnostic and radiotherapeutic agents is needed.

It would be useful to have a method of radiolabeling the peptide directly without the use of a separate chelating ligand and the peptide linkage group. This would alleviate some of the difficulties currently observed with the incorporation of these functionalities, such as lowered ED50 values and increased nonspecific localization.

SUMMARY OF THE INVENTION

According to the present invention, there is provided a compound for use as a diagnostic or therapeutic pharmaceutical consisting essentially of an alpha-melanotropin stimulating hormone analog which has integrally located a radionuclide. The radiolabeled alpha-melanotropin is administered to the body in an amount sufficient to allow uptake and retention by the tumor cells.

DESCRIPTION OF THE DRAWINGS

Other advantages of the present invention will be readily appreciated as the same becomes better understood by reference to the following detailed description when considered in connection with the accompanying drawings wherein.

The file of this patent contains at least one drawing executed in color. Copies of this patent with color drawing

DETAILED DESCRIPTION OF THE INVENTION

Figure 1:
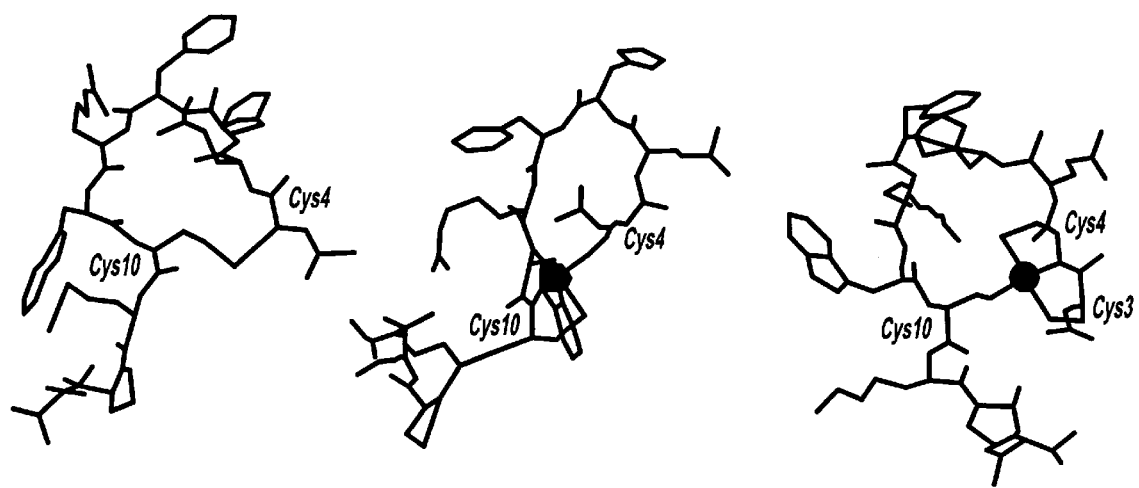
FIG. 1 depicts the chemical structure of the alpha-meloantropin hormone stimulating analogs.

Generally, the present invention provides a compound for use as a diagnostic or therapeutic pharmaceutical and method of using the same; however, they may also be used for other pharmaceutical applications. Alpha melanocyte stimulating hormone (α-MSH) is a tridecapeptide [Ac-Ser-Tyr-Ser-Met-Glu-His-Phe-Arg-Trp-Gly-Lys-Pro-Val-NH$_2$] that regulates skin pigmentation in most vertebrates (Hruby, V. J., 1993). The core α-MSH sequence His-Phe-Arg-Trp, conserved in a number of species, has been found to be sufficient for receptor recognition (Hruby, V. J., 1993). The presence of α-MSH receptors on both murine and human melanoma cells (Tatro, J. B., 1989; Siegrist, W., 1989) suggests that α-MSH analogs might be developed into targeted imaging or therapeutic agents. Several analogs of a-MSH have been radiolabeled either with halogens or with transition metal radionuclides coordinated by bifunctional chelates (Bard, D. R., 1990; Bagutti, C., 1994; Garg, P. K., 1996; Vaidyanathan, G., 1997).

More specifically, the present invention provides $^{188}$Re or $^{99m}$Tc radiolabeled α-MSH analogs in which metal coordination is an integral part of the molecules' structure. It was hypothesized that cyclic α-MSH analogs, engineered to incorporate radionuclides directly into their structures, would display exceptional stability, biodistribution, and tumor targeting properties. Rhenium bound α-MSH analogs were synthesized and characterized to determine if different metal incorporation strategies resulted in molecules with varying structural stabilities and bioactivities.

Incorporation of Re into an initial α-MSH analog resulted in decreased stability and receptor affinity. Structural characterization of the Re bound α-MSH complex indicated that metal coordination dramatically altered the core receptor binding sequence. Correlation of structural changes with functional changes in the initial Re bound α-MSH complex provided the foundation for the design of a second generation ReCCMSH analog with greatly improved stability and bioactivity. Initial in vivo tumor targeting experiments show that the corresponding $^{99m}$TcCCMSH analog is able to image melanoma in a murine tumor model system. These results indicate that $^{99m}$Tc- and $^{188}$Re-CCMSH analogs have potential as melanoma imaging and therapeutic agents.

The results demonstrate that the application of structure based molecular design in the development of α-MSH receptor-avid peptides that were cyclized through the coordination of the transition metals Re and Tc. Several cycles of peptide design, synthesis, structural analysis, and functional characterization were employed to develop α-MSH analogs that incorporated Re and Tc into their structures while retaining high affinity for their cognate receptors present on melanoma cells. That the $^{99m}$TcCCMSH analog was able to target melanoma in a murine tumor model system demonstrated the use of these compounds for melanoma imaging or therapy. The compounds are generally of the formula:

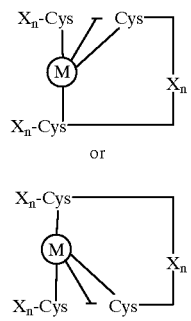

where X=any amino acid, n=1 to 1000, and M=transition metal.

or

Z—Cys—Cys—X$_n$—Cys—Y or

Z—Cys—X$_n$—Cys—Cys—Y where all three Cys—SH groups are involved in metal coordination.

The radionuclide bound α-MSH complex is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to elimination of all cancer cells and to improved survival rate or more rapid recovery, or improvement or elimination of symptoms and other indicators as are selected as appropriate measures by those skilled in the art.

In the method of the present invention, the radionuclide bound α-MSH complex can be administered in various ways. It should be noted that the radionuclide bound α-MSH complex can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, as well as intrathecal and through infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice exemplified herein which treatment has a length proportional to the length of the disease process and drug effectiveness. The doses may be single doses or multiple doses over a period of several days. The treatment generally has a length proportional to the length of the disease process and drug effectiveness and the patient species being treated. Optimal dosing schedules may be calculated using measurements of drug accumulation in the body. Practitioners of ordinary skill in the art can readily determine optimum dosages, dosing methodologies, and repetition rates. Optimum dosages may vary depending on the relative potency of radionuclide bound α-MSH complex, and can generally be determined based on $ED_{50}$ values in in vitro and in vivo animal studies and clinical trials.

When administering the radionuclide bound α-MSH complex parenterally, the radionuclide bound α-MSH complex will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the radionuclide bound α-MSH complex can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. No. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the radionuclide bound α-MSH complex utilized in the present invention can be administered orally to the patient. Conventional methods such as administering the compounds in tablets, suspensions, solutions, emulsions, capsules, powders, syrups and the like are usable.

Known techniques which deliver the radionuclide bound A-MSH complex orally, subcutaneously or parenterally including intravenous, intraarterial, intramuscular, and intraperitoneally as well as intrathecal techniques and retain the biological activity are preferred.

For delivery within the CNS, intrathecal delivery can be used with for example an Ommaya reservoir. U.S. Pat. No. 5,455,044 provides for use of a dispersion system for CNS delivery or see U.S. Pat. No. 5,558,852 for a discussion of CNS delivery. In addition, pharmacological formulations that cross the blood-brain barrier can be administered. [Betz et al., 1994; Brem et al., 1993] Such formulations can take advantage of methods now available to produce chimeric peptides in which the present invention is coupled to a brain transport vector allowing transportation across the barrier [Pardridge, et al., 1992; Pardridge, 1992; Bickel, et al., 1993]. Further, in appropriate cases blood-brain barrier disruption can be utilized [Neuwelt et al., 1980].

In one embodiment, the radionuclide bound α-MSH complex can be administered initially by intravenous injection to bring blood levels of radionuclide bound α-MSH complex to a suitable level. The patient's radionuclide bound α-MSH complex levels are then maintained by an oral dosage form, although other forms of administration, dependent upon the patient's condition and as indicated above, can be used. The quantity of radionuclide bound α-MSH complex to be administered will vary for the patient being treated and will vary from about 100 ng/kg of body weight to 100 mg/kg of body weight per day and preferably will be from 10 μg/kg to 10 mg/kg per day.

The above discussion provides a factual basis for the use of α-melanocyte stimulating hormone analogs radiolabeled with Re and Tc. The methods used with and the utility of the present invention can be shown by the following non-limiting examples.

EXAMPLES

Materials and Methods

Synthesis and Purification of Peptide-Metal Complexes.

The peptides NA-Cys-Glu-His-D-Phe-Arg-Trp-Cys-Lys-Pro-Val-NH$_2$(Cody, W. L., 1985) and NAc-Cys-Cys-Glu-His-D-Phe-Arg-Trp-Cys-Lys-Pro-Val-NH$_2$ were synthesized using standard Fmoc chemistry. ReMSH was synthesized using the exchange complex ReOCl$_3$(Me$_2$S) (OPPh$_3$) (Grove, D. E., 1966; Bryan, J. C., 1987) by incubation of 1:1 peptide:exchange complex in 62% MeOH, pH=8–9 at 65–70° C. for one hour. ReCCMSH was synthesized using the exchange complex Re-glucoheptonate by incubation of 1:1 peptide:exchange complex in 62% MeOH, pH=8–9 at 65–70α C. for one hour. Both complexes were purified by C18 reverse phase HPLC. ReMSH was further purified by normal phase HPLC using a polysulfoethyl aspartamide column from PolyLC Inc. Both complexes underwent Ellman's analysis to test for the presence of free sulfhydryl groups (Ellman, G. L., 1959). The identity of ReCCMSH was confirmed by ESI-MS at Mallinckrodt Inc., St. Louis, Mo.: m/z (M+H)$^+$ obs.=1648.1, calc.=1647.9. The identity of ReMSH was confirmed by FAB-MS at the University of Kansas mass spectrometry facility: m/z (M+H)$^+$ obs.=1546, calc.=1544.8.

$^{99m}$TcO$_4$$^-$ was obtained from a $^{99}$Mo/$^{99m}$Tc generator produced by Mallinckrodt, Inc. $^{188}$Re was obtained from a $^{188}$W/$^{188}$Re generator produced by the University of Missouri research reactor. Radiolabeled peptides were prepared by substitution onto either $^{99m}$Tc- or $^{188}$Re- glucoheptonate. For $^{188}$Re complexes, 500 µL of generator eluant was added to a tube containing 50 mg Na-glucoheptonate and 10 mg SnCl$_2$·2H$_2$O dissolved in 200 µL N$_2$-purged 5% disodium-EDTA and heated at 70–80° C. for 0.5 hour. 50 µL of a 1 mg/mL peptide solution was then added, the pH was adjusted to 7–8 with 0.5 N NaOH, and the mixture was allowed to incubate for 90 minutes. at 70–80° C. Syntheses of $^{99m}$Tc-labeled peptides differed only in that they were carried out at 25° C. using a 10-fold lower concentration of SnCl$_2$·2H$_2$O. Radiolabeled complexes were analyzed by coinjection on a C18 reverse phase-HPLC column, and in all cases were found to coelute with the previously characterized nonradioactive standards.

NMR Data Collection and Processing.

NMR data were collected on a 500-MHz Bruker AMX or DMX spectrometer and processed on a Silicon Graphics Inc. (SGI) XZ4000 workstation using the SYBYL program (Tripos, Inc.). The $^1$H data were collected in 90%H$_2$O/10%D$_2$O at concentrations ranging from 4–10 mg/mL. All spectra were recorded using the time-proportional phase incrementation (TPPI) method. In most cases, the spectral width was 6000 Hz. Typically the data set size was 2048 (t$_2$)×256(t$_1$) blocks with between 16–64 scans/fid. TOCSY spectra were collected using an 80 ms mixing time; the NOESY and ROESY mixing time was 200 ms.

For APOMSH and ReMSH experiments, H$_2$O suppression was carried out using the WATERGATE pulse sequence (Piotto, M., 1992). A 1—1 jump return sequence was used in some 1D experiments for H$_2$O suppression. Data sets were multiplied by a 0–90° shifted sinebell squared transformation function and zerofilled to 1024k in t$_1$ prior to Fourier transformation. 2D spectra for the peptide-metal complexes were collected at 298K. For APOMSH, additional 2D spectra were collected at 278K. $^3J_{\alpha NH}$ data were gathered from resolution enhanced 1D spectra for each compound. Temperature gradient studies spanned 278K–308K for each compound.

Molecular Modeling.

Molecular modeling studies were performed on an SGI XZ4000 workstation using the SYBYL program. For each complex, random starting structures were generated from restrained MD simulations in vacuo, using a single distance restraint between thiol sulfurs to initially close the ring. Modeling of metal coordination was based on small molecule structures from the Cambridge Crystallographic Database (Grummon, G., 1995; Hansen, L., 1992; Rao, T. N., 1991). Charges were not included in the modeling of peptide-metal complexes. The metal coordination sphere was maintained via a system of interrelated geometrical restraints. Peptide models consistent with NMR-derived distance restraints were obtained by sequential application of restrained molecular dynamics and minimization using the Powell method (Powell, M. J. D., 1977). Conformational searches were carried out using a simulated annealing protocol. The APOMSH structures were heated to 2000K, then cooled to 300K. Metal-bound structures were only heated to 800K due to the highly restrained nature of the metal center. Structures emerging from simulated annealing runs were minimized to convergence (gradient<0.05 kcal/mol*Å) and compared using the FIT algorithm within SYBYL.

Bioactivity and Receptor Binding Assays.

Peptide bioactivity was determined by measuring melanin released into cell culture media in an in vitro assay using B16Fl murine melanoma cells (Siegrist, W., 1986). Cells were incubated with various concentrations of peptide and assayed for melanin production by measuring the absorbance of the culture media at 405 nm. Absorbance values were compared to a standard curve obtained using synthetic melanin from Sigma. The standard curve was linear over the experimental range of absorbance values.

Quantitative receptor binding assays were carried out following a previously described method (Siegrist W., 1988; Sahm, U. G., 1994). Cells were seeded at a density of 5×10$^5$ cells per well in 24 well tissue culture plates and exposed to varying concentrations of peptides on 0.5 mL of binding media (25 mM HEPES/NaOH pH=7.4, 0.2c BSA, 0.3 mM 1,10-phenanthroline, and approximately 100,000 CPM of $^{125}$I-[Nle$^4$, D-Phe$^7$]-α-MSH) (36) at 4° C. for 8 hours. The cells were rinsed with PBS, lysed with 1 M NaOH and counted in a 1275 minigamma gamma counter from LKB Wallac.

Imaging Studies.

Six week old C57BL/6 mice (Harlan, Sprague, Dawley, Inc.) were injected in the right flank with 1×10$^6$ B16-Fl mouse melanoma cells. Tumors, approximately 200–400 mgs, appeared 10 days post injection. Each mouse was given 25 µCi of $^{99m}$TcCCMSH by tail vein injection. The mice were sacrificed thirty minutes post injection and the images were acquired by a Prism XP3000 triple head γ camera (Picker, Inc.) equipped with a low-energy high resolution parallel collimator. The images were collected on a 512 matrix with 3.999 magnification.

Biodistributions.

The biodistribution and pharmacokinetics of the $^{99m}$Tc and $^{188}$Re labeled cyclic α-MSH peptide analogue (CCMSH) were examined in a C57BL/6 murine melanoma animal model. 1×10$^6$ B16-Fl melanoma cells were injected subcutaneously to induce tumor formation. Tumors, 200–400 milligrams in weight, appeared approximately 10 days post injection. Normal and tumor bearing mice were injected with 2–3 µCi of $^{99m}$Tc or $^{188}$Re labeled CCMSH. At various times post-injection the mice were sacrificed and the individual tissues were counted.

Results and Discussion

Metal-binding Site Design.

Molecular modeling was used to design and evaluate cyclic α-MSH analogs for their potential to incorporate Re or Tc into their structures. Several different factors were taken into account in the design of rhenium- and technetium-binding sites, including metal coordination geometry, donor atom selection, and peptide conformation. Both Tc and Re, when in the +5 oxidation state, prefer a square pyramidal coordination geometry. Structural studies of small organic complexes of these metals have shown that donor atoms are located at the corners of a square plane, with a monooxo group of located above, at the apex of a square pyramid (Grummon, G., 1995; Hansen, L., 1992; Rao, T. N., 1991).

Another determinant of the metal-binding site was the known preference of these metals for specific donor atoms (i.e. S>N>>O) (Vanbilleon, H. P., 1995).

A third important factor was determined not by the metal, but by the structure of the peptide itself. The metal binding site must be engineered so that metal coordination does not disrupt the biologically active conformation of the molecule. The cyclic α-MSH analog Cys$^{4,10}$, D-Phe$^7$-α-MSH$_{4-13}$ (Cody, W. L., 1985) was used as the starting point of our studies. Cys$^{4,10}$, D-Phe$^7$-α-MSH$_{4-13}$ (APOMSH) retains a core sequence of residues, His-D-Phe-Arg-Trp, which has been found to be sufficient for the bioactivity of a α-MSH (Hruby, V. J., 1993). In the development of this peptide it was found that cyclization and incorporation of a D-amino acid in position 4 both increased the potency and prolonged the biological effect of this analog relative to wild-type-α-MSH (Cody, W. L., 1985).

Initial Rhenium Complexation.

The cyclic rhenium α-MSH analog ReMSH was synthesized by incorporation of a Re(V)O core into APOMSH. Rhenium was introduced into a pre-reduced sample of APOMSH via transchelation from $ReOCl_3(Me_2S)$ $(OPPh_3)$. A FAB-MS spectrum confirmed the expected molecular weight of a 1:1 peptide:metal complex. Initial 2D NMR studies of ReMSH showed that 2 amide proton resonances were absent compared to the metal-free peptide. The two amide $^1H$ resonances missing in the ReMSH spectrum were assigned to Trp9 and Cys10 (Table 1). These results suggested that the thiolate sulfur of Cys10 and the two preceding amide nitrogens form three corners of a square plane of donor atoms.

Chemical shift alterations of Cys4βH's, as well as Ellman's analysis, showed that the fourth donor atom in the coordination sphere of rhenium was the thiolate sulfur of Cys4. As a result of this binding geometry, ReMSH possesses three metal-containing rings, two five-membered rings and one eighteen-membered ring (FIG. 1). Thus, the ring size of ReMSH was reduced from a 23-membered ring in APOMSH to an 18-membered ring.

The ReMSH metal coordination geometry included the amide nitrogen of Trp, which is a member of the core sequence of residues responsible for α-MSH binding to its receptor. Some decomposition of the ReMSH complex was observed by NMR over time. Ellman's analysis of ReMSH NMR samples revealed that approximately 3% of the cysteine residues within the molecule were present as free thiols.

To analyze the structural effects of rhenium incorporation into the α-MSH analogs, NOESY spectra of both APOMSH and ReMSH were examined and sequential and nonsequential NOE's were identified. For each compound, NOE derived distance restraints were grouped into either strong, medium, or weak categories based on their intensities. These restraints were then applied to randomly generated starting structures within SYBYL. In modeling the ReO core, geometrical restraints (range, angle, and torsion) were employed in conjunction with a pseudoatom representing the rhenium metal. The geometric restraints were optimized to maintain a square planar array of donor atoms in a model rhenium-peptide compound (Cys-Gly-Cys). Previous structural analysis demonstrated that the tetrapeptide NAc-Cys-Gly-Cys-Gly formed a stable $N_2S_2$ Re chelate (Giblin, M. F., 1997). Refinement of α-MSH models was carried out using a restrained molecular dynamics/simulated annealing protocol, followed by restrained energy minimization. In each case, the average structure from the final MD cycle was found to have no range violations greater than 0.1 Å.

For the ReMSH molecule, 20 cycles of MD/annealing/minimization converged to a single family of structures, with backbone RMSD's ranging between 0.86–1.26 Å. Compared with the APOMSH structures, the ReMSH NMR structures converged to a much more tightly defined family which included a reverse turn centered on residues Glu5-His6. The higher degree of definition was due to a cross ring NOE between Cys4NH and Arg8αH not present in APOMSH and the smaller ring size of ReMSH. As with APOMSH, high values for temperature dependencies of amide $^1H$ chemical shifts indicated that no intramolecular hydrogen bonds were present to stabilize the turn. $^3J_{\alpha NH}$ values for ReMSH were systematically lower than for APOMSH, indicative of greater restraint in the peptide backbone of ReMSH due to its smaller ring size. Distortion of the ReMSH backbone relative to the APOMSH structures lead to differences in the presentation of core sequence sidechains. Rather than being located on the same face of the molecule distributed along a reverse turn, His, D-Phe and Trp sidechains were displayed along an extended backbone segment.

Figure 2A:
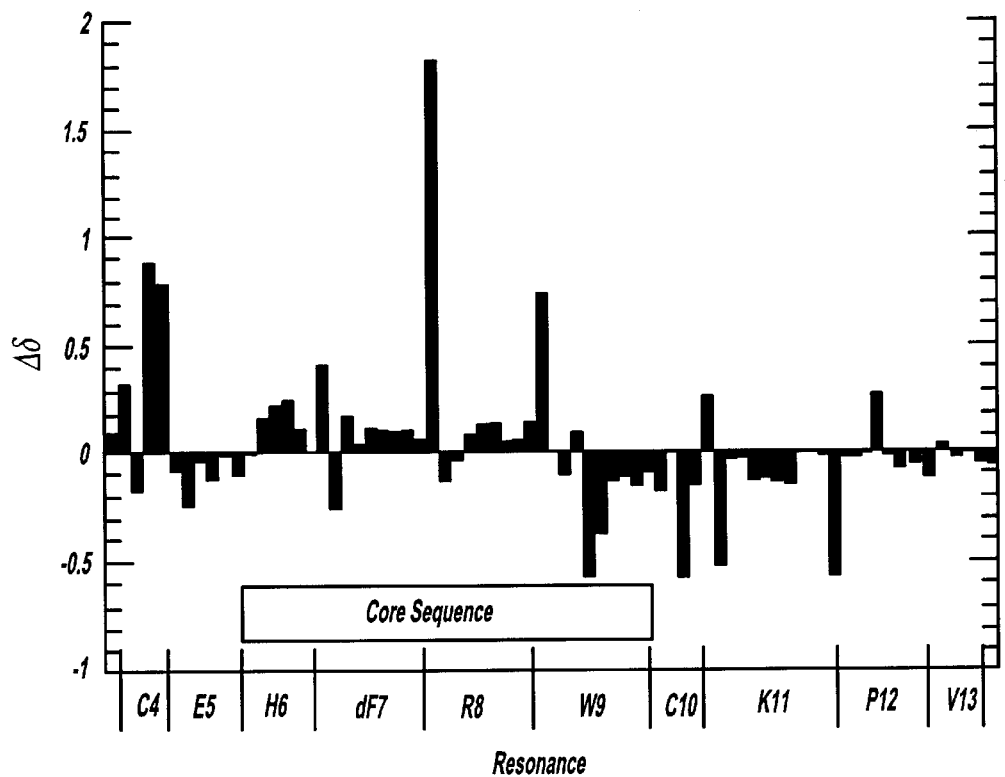
FIG. 2 is graphs showing the chemical shift changes upon rhenium binding to two α-MSH analogs; the changes in chemical shift being calculated according to the formula $\Delta\delta = (\delta_{metal-bound} - \delta_{metal-free})$; a high degree of chemical shift disruption being seen within the core receptor recognition sequence in ReMSH (A); ReCCMSH (B) showing a much lesser degree of chemical shift disruption of core sequence residues, while metal-coordinating residues bracketing the core sequence are highly disturbed.
Figure 2B:
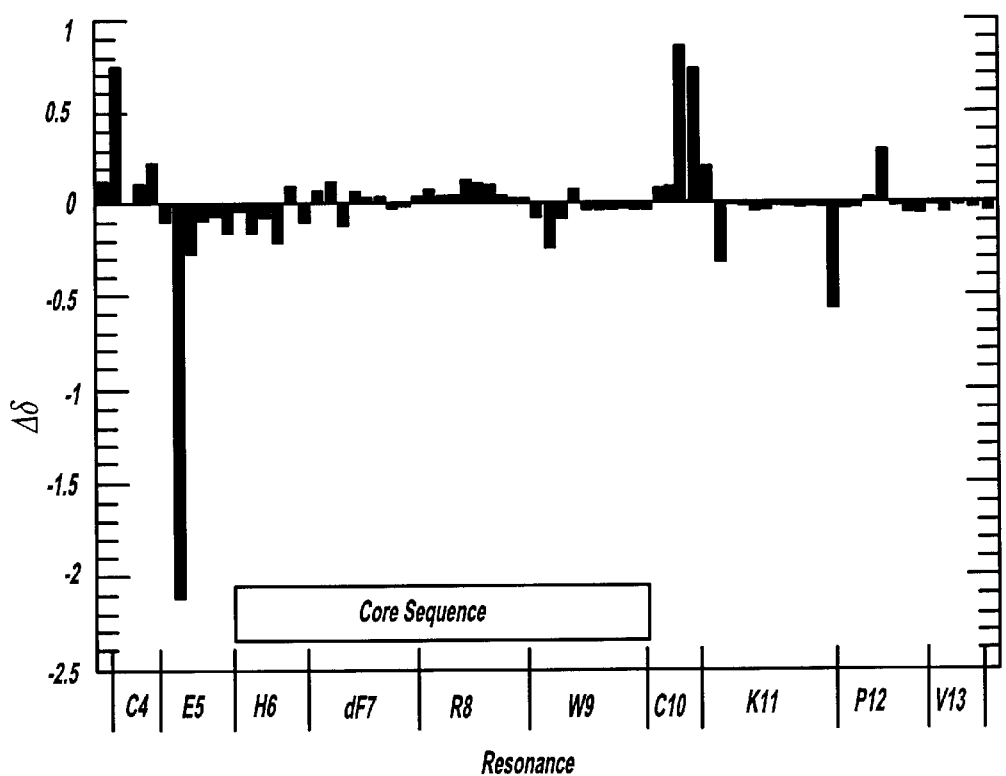

The proximity of key residues within ReMSH to the metal center resulted in profound changes in their chemical environment in solution. The $^1H$ chemical shift changes that occurred upon metal coordination are shown graphically in FIG. 2. Large chemical shift differences were expected for residues involved in metal-binding. For ReMSH, however, pronounced chemical shift changes occurred not only for coordinating residues, but also for other residues within the core sequence. NMR and crystallographic studies of monooxo Re(V) complexes have shown that protons oriented syn relative to the metal-oxo group are generally deshielded, while protons in an anti configuration are often shielded (Lever, S. Z., 1990). Alpha proton resonances of Arg and Trp were both highly deshielded, and Trp sidechain resonances were shielded. The closeness of the metal center to the Arg and Trp residues, most notably the Trp sidechain, may have contributed to the low receptor affinity of ReMSH.

The ReMSH model structures were strained due to the restraints imposed by Trp9N and Cys4S metal coordination. This increased strain was reflected experimentally in the low stability of the ReMSH molecule. As assessed by NMR, approximately 20% of the original ReMSH species had degraded after a 24 hour period. The decay of the ReMSH complex most likely represented a rearrangement of the donor atoms in the metal coordination sphere to relieve the strain introduced into the molecule by the Cys4 sulfur coordination. Release over time of the Cys4 sulfur as a free thiolate would be consistent with the Ellman's analysis of the ReMSH complex. The same trends in stability were observed at the tracer level. Synthesis of $^{99m}Tc/^{188}ReMSH$ confirmed the relatively low stability of ReMSH. Table 2 shows that in competition with 10 mM free cysteine, the $^{188}ReMSH$ complex has a $t_{1/2}$ of approximately 4 hours. The analogous $^{99m}TcMSH$ complex had an even shorter half-life, with a $t_{1/2}$ of less than 2 hours, consistent with an increased lability of Tc to substitution reactions.

The effect of metal incorporation on the bioactivity and receptor binding affinity of ReMSH is shown in Table 3. The bioactivities of APOMSH and the ReMSH complex were assayed by measuring stimulation of melanin production by B16-F1 murine melanoma cells. The $EC_{50}$ values for melanin synthesis by APOMSH and ReMSH were $2.6 \times 10^{-11}$ and $5.4 \times 10^{-10}$, respectively. Incorporation of rhenium into ReMSH resulted in approximately a 20-fold decrease in the ability of the molecule to stimulate melanin production compared to APOMSH. Receptor binding assays were performed with APOMSH and ReMSH on B16-F1 murine melanoma cells. A decrease was observed in the ability of the ReMSH analog to displace an $^{125}I$-labeled α-MSH analog from the cells in a competitive receptor binding assay (Table 3). The $K_i$ for the ReMSH complex was $6.6 \times 10^{-8}$ which reflected an apparent 100 fold decrease in receptor binding affinity compared to APOMSH ($K_i=6.8 \times 10^{-10}$). Therefore, it appeared that the presence of the Re(V)O core or its effect on the solution structure of ReMSH significantly reduced the molecule's receptor affinity and biological activity.

Metal Binding Site Redesign.

Two different approaches were followed to create rhenium-MSH conjugates with improved receptor binding and bioactivity profiles. Structural information relating to ReMSH indicated that the metal-binding site was too close to residues essential for receptor binding. In one attempt to distance the metal-binding site from the His-D-Phe-Arg-Trp core sequence, a spacer Gly residue was inserted between the Trp residue and the C-terminal Cys. It was hypothesized that the addition of the Gly residue would displace the crucial Trp residue from the metal coordination sphere. The compound was synthesized using the same conditions used for the synthesis of ReMSH and resulted in a complex which appeared by FAB-MS to contain 2 rhenium-oxo groups per peptide molecule. Receptor binding data on this 2:1 rhenium:peptide complex showed no increase in binding affinity over ReMSH (data not shown). That this dimeric complex was the major product of two separate syntheses suggested that there may be an entropic barrier to the cyclization of larger rings via an Re(V)O core.

The second approach to generate a rhenium-MSH complex with increased receptor binding affinity involved the synthesis of an analog of APOMSH which contained an additional N-terminal Cys residue, termed Cys3. It was hoped that inclusion of this additional thiolate would drive the metal coordination sphere away from the His-D-Phe-Arg-Trp core sequence, by taking advantage of the increased affinity of Re and Tc for sulfur donor atoms over nitrogen. NMR characterization of this rhenium complex (ReCCMSH) indicated that only a single amide proton resonance had been lost upon Re complexation. The single amide $^1$H resonance lost in ReCCMSH was assigned to Cys4. Ellman's analysis of ReCCMSH revealed no free thiols present in the peptide-metal complex, suggesting that, as with ReMSH, all thiolates were involved in metal coordination. An ESI-MS spectrum confirmed the expected molecular weight of a 1:1 peptide:metal complex. In this case, the two N-terminal Cys thiolates in combination with the intervening amide nitrogen formed three corners of a square plane. The final donor atom was again the remaining thiolate, resulting in cyclization of the molecule. ReCCMSH was also a tricyclic molecule, with rings of 6, 5, and 24 members, respectively (FIG. 1). The size of the ring containing the core sequence of residues had increased by 6 atoms when compared with ReMSH.

The chemical shift disruption of core sequence resonances of ReCCMSH was far less pronounced than in ReMSH (FIG. 2), indicating that the disposition of core sequence residues was similar to that in APOMSH. That the major chemical shift changes in ReCCMSH were associated with the resonances of Cys4, Glu5, and Cys10 indicated that the metal-binding site was successfully moved away from the His-D-Phe-Arg-Trp core receptor binding sequence.

Compared with ReMSH, ReCCMSH displayed increased flexibility due to its larger ring size. Sequential NH—NH NOE's were observed in the region of the backbone between Glu5 and Arg8, indicating the presence of a reverse turn. However, broadening and overlap of amide resonances suggested that conformational exchange between more than one structure was occurring. Increasing the temperature to 313K sharpened and resolved the His6, Arg8, Trp9, and Cys10 resonances. Use of a jump-return sequence in place of presaturation for $H_2O$ suppression did not affect the magnitude of these amide resonances, indicating that conformational and not chemical exchange was responsible for this broadening. The increased flexibility of the 24-membered ring was reflected in increased backbone RMSD's between structures resulting from the MD/simulated annealing protocol.

The $^{99m}$Tc- and $^{188}$Re-labeled analogs of ReCCMSH were virtually inert to substitution in 10 mM Cys competition assays, while the $^{99m}$Tc- and $^{188}$Re-labeled analogs of ReMSH were readily exchanged under the same assay conditions (Table 2). This increased stability of ReCCMSH probably resulted from the presence of an additional sulfur donor atom and from decreased backbone strain in the molecule due to the increased ring size. Both the bioactivity and receptor binding affinity of ReCCMSH were greatly improved relative to ReMSH. The ability of the ReCCMSH analog to stimulate melanin production was almost identical to APOMSH (Table 3). The ReCCMSH analog exhibited a receptor binding affinity of 2.9 nM, which was approximately 25-fold higher than that of ReMSH (Table 3). Redesign of the Re coordination site in ReCCMSH appeared to relieve internal steric constraints within the core receptor binding sequence that resulted in greatly improved radiochemical stability and receptor affinity.

In vivo Biodistribution and Tumor Targeting.

The biodistribution and pharmacokinetics of the $^{99m}$Tc and $^{188}$Re labeled CCMSH were examined in a murine melanoma animal model. Both the $^{99m}$Tc-CCMSH and $^{188}$Re-CCMSH analogues showed rapid clearance, with the kidneys acting as primary route of excretion (Tables 4 and 5). In melanoma bearing mice, the $^{99m}$Tc-MCCMSH molecule accumulated rapidly in the tumor and remained at 10.88±0.54% dose/gram out to 4 hours (Table 4). The $^{188}$Re-CCMSH analogue also showed rapid tumor uptake in melanoma bearing mice with no significant accumulation in any vital organ (Table 5). The percent dose/gram tumor uptake of the $^{188}$Re-CCMSH analogue was 10.89±2.27 at 0.5 hours, and 3.24±0.63 at 12 hours. By 24 hours the tumor dose/gram was 1.72±0.39% with a tumor/blood ratio of 207.90.

Figure 3:
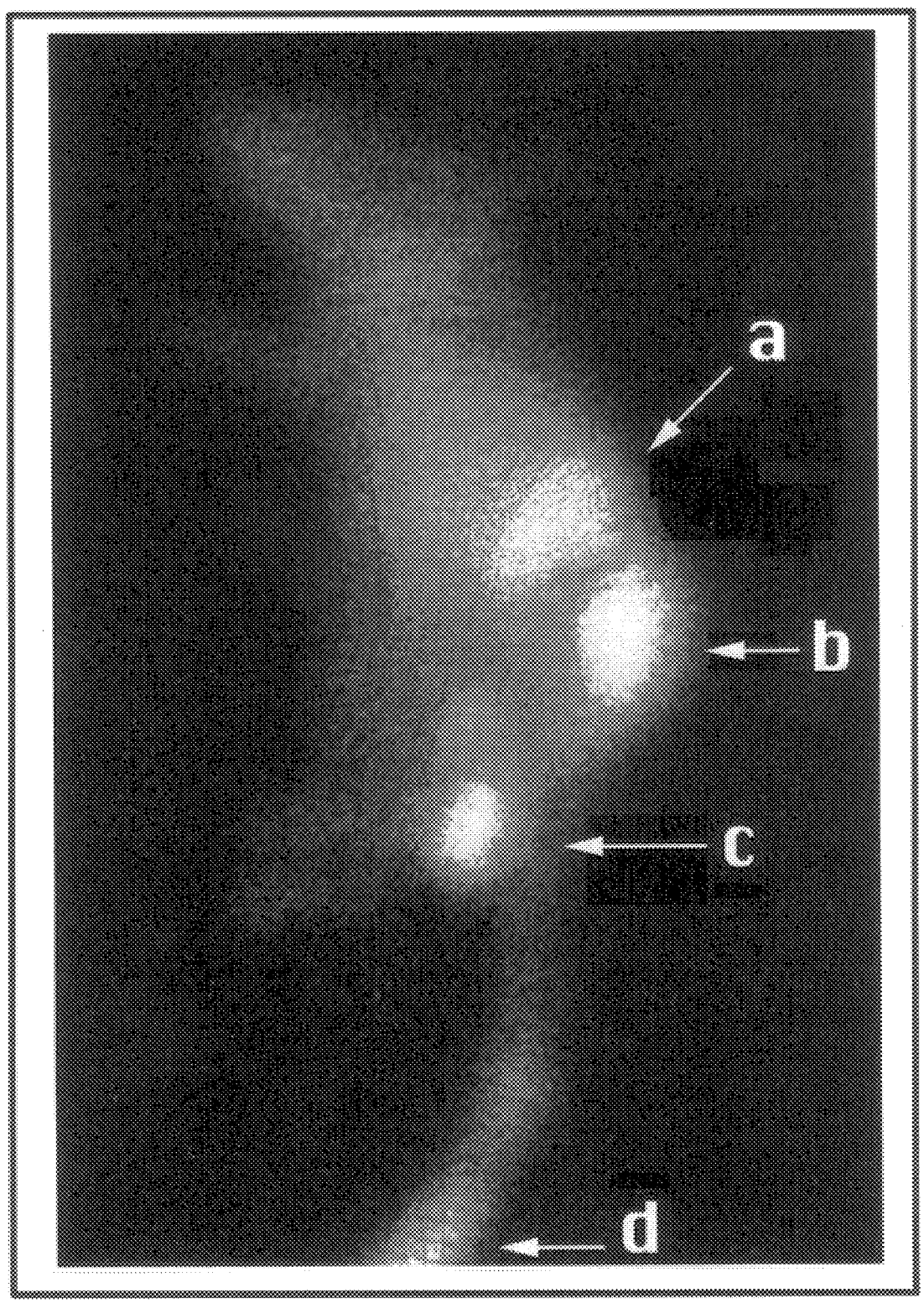
FIG. 3 is an image of a melanoma tumor in a mouse injected with TcCCMSH; the γ-camera image of the melanoma bearing mouse being acquired 30 minutes post injection and the lateral image of the mouse with a 400 milligram tumor shows a high degree of radioactivity localized in the tumor (b) with lesser amounts present in the kidneys (a), bladder (C), and tail vein injection site (d); the intensity of the γ-emission being color coded high to low, ranging from white-yellow through orange, with dark red representing lowest values.

In vivo tumor localization. The ability of $^{99m}$Tc labeled CCMSH to target solid melanoma tumors in vivo was examined in a C57BL/6 mouse model. 25 µCi of $^{99m}$TcCCMSH was injected into the tail vein of a mouse bearing a 0.4 gram melanoma tumor in the right flank. Anterior and lateral scintigraphic images of the mouse were acquired 30 minutes post injection. Significant accumulation of the $^{99m}$Tc-labeled peptide was clearly visible in the melanoma tumor (FIG. 3). These results show that the $^9$9mTc-CCMSH analog was capable of imaging melanoma tumors in vivo. Radioactivity was also present in the kidneys and bladder, which are the primary route for peptide excretion. A $^{99m}$Tc-labeled bombesin peptide analog was also injected into a tumor-bearing mouse as a control for peptide targeting specificity. The radiolabeled bombesin analog did not display selective tumor uptake (data not shown). In conclusion, the data presented in this application results demonstrated that the redesigned $^{99m}$TcCCMSH molecule was capable of selectively targeting melanoma tumors in vivo. Detailed distribution studies are underway with the $^{99m}$Tc- and $^{188}$Re-labeled CCMSH analogs exhibit rapid tumor uptake, superior tumor residency and efficient whole body clearance.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

$^1$H chemical shift values for the three α-MSH analogs.

| Resonance | APOMSH | ReMSH | ReCCMSH |
|---|---|---|---|
| ACE.H | 1.96 | 2.06 | 2.08 |
| C3.Hα | a | a | 5.01 |
| C3.HN | a | a | 8.44 |
| C3.Hβ | a | a | 2.93, 3.36 |
| C4.Hα | 4.69 | 5.00 | 5.43 |
| C4.HN | 8.42 | 8.26 | b |
| C4.Hβ | 3.05,3.16 | 3.92,3.92 | 3.16,3.38 |
| E5.Hα | 4.22 | 4.15 | 4.15 |
| E5.HN | 8.88 | 8.64 | 6.76 |
| E5.Hβ | 1.84,1.92 | 1.81,1.81 | 1.56,1.84 |
| E5.Hγ | 2.13,2.21 | 2.12,2.12 | 2.06,2.06 |
| H6.Hα | 4.51 | 4.51 | 4.47 |
| H6.HN | 8.27 | 8.42 | 8.11 |
| H6.Hβ | 3.00,3.14 | 3.19,3.35 | 2.92,2.92 |
| H6.HC4 | 8.43 | 8.53 | 8.50 |
| H6.HC2 | 7.13 | 7.13 | 7.02 |
| dF7.Hα | 4.53 | 4.91 | 4.58 |
| dF7.HN | 8.29 | 8.03 | 8.37 |
| dF7.Hβ | 2.94,3.07 | 3.09,3.09 | 2.81,3.10 |
| dF7.Hδ | 7.19 | 7.28 | 7.18 |
| dF7.Hε | 7.25 | 7.33 | 7.22 |
| dF7.Hζ | 7.33 | 7.37 | 7.32 |
| R8.Hα | 4.22 | 6.01 | 4.25 |
| R8.HN | 7.99 | 7.85 | 8.00 |
| R8.Hβ | 1.44,1.52 | 1.39,1.58 | 1.45,1.60 |
| R8.Hγ | 1.13,1.13 | 1.23,1.23 | 1.20,1.20 |
| R8.Hδ | 2.98,2.98 | 3.01,3.01 | 2.99,2.99 |
| R8.Hε | 7.05 | 7.16 | 7.04 |
| W9.Hα | 4.72 | 5.41 | 4.63 |
| W9.HN | 8.27 | b | 8.00 |
| W9.Hβ | 3.25,3.25 | 3.13,3.32 | 3.15,3.29 |
| W9.H2 | 7.28 | 6.69 | 7.25 |
| W9.H4 | 7.65 | 7.26 | 7.62 |
| W9.HIm | 10.1 | 9.98 | 10.1 |
| W9.H5 | 7.15 | 7.13 | 7.12 |
| W9.H7 | 7.49 | 7.32 | 7.46 |
| W9.H6 | 7.25 | 7.01 | 7.22 |
| C10.Hα | 4.63 | 4.44 | 4.66 |
| C10.HN | 8.07 | b | 8.10 |
| C10.Hβ | 3.00,3.17 | 2.40,3.00 | 3.80,3.86 |
| K11.Hα | 4.40 | 4.62 | 4.54 |
| K11.HN | 8.16 | 7.60 | 7.79 |
| K11.Hβ | 1.78,1.78 | 1.72,1.72 | 1.77,1.77 |
| K11.Hγ | 1.45,1.45 | 1.30,1.30 | 1.39,1.39 |
| K11.Hδ | 1.69,1.69 | 1.52,1.52 | 1.65,1.65 |
| K11.Hε | 3.01,3.01 | 3.00,3.00 | 2.98,2.98 |
| K11.Hζ | 8.10 | 7.49 | 7.49 |
| P12.Hα | 4.45 | 4.42 | 4.41 |
| P12.Hβ | 1.93,2.01 | 1.89,1.99 | 1.89,2.02 |
| P12.Hγ | 2.07,2.30 | 2.28,2.28 | 2.29,2.29 |
| P12.Hδ | 3.67,3.82 | 3.59,3.77 | 3.63,3.78 |
| V13.Hα | 4.05 | 3.92 | 4.04 |
| V13.HN | 8.23 | 8.26 | 8.15 |
| V13.Hβ | 2.05 | 2.04 | 2.03 |

TABLE 1-continued $^1$H chemical shift values for the three α-MSH analogs.

| Resonance | APOMSH | ReMSH | ReCCMSH |
|---|---|---|---|
| V13.Hγ | 0.970 | 0.970 | 0.950 |
| AMD.HN2 | 7.14 | 7.10 | 7.11 |
| AMD.HN1 | 7.67 | 7.63 | 7.64 | a. No Cys3 residue in this analog.

b. Amide nitrogen deprotonated upon metal coordination.

TABLE 2

Stabilities of tracer level complexes.

| | Challenge | | | |
|---|---|---|---|---|
| | 10 mM Cysteine[b] | | 0.05 M Phosphate | |
| Compound[a] | 4 hrs | 24 hrs | 4 hrs | 24 hrs |
| $^{188}$ReMSH | 48.9% | 34.0% | 90.3% | 66.4% |
| $^{99m}$TcMSH | 30.7% | 6.0% | 50.8% | 33.0% |
| $^{188}$ReCCMSH | 99.9% | 96.7% | 99.9% | 99.9% |
| $^{99m}$TcCCMSH | 95.0% | 91.0% | 99.9% | 99.9% |

[a]Compounds were identified based on reverse phase HPLC coelution with characterized nonradioactive standards.

[b]The 10 mM cysteine challenge was prepared by diluting the tracer level reaction mix 1:2 into 20 mM cysteine at t = 0.

TABLE 3

$EC_{50}$ and $K_i$ values for various α-MSH analogs.

| compound | $K_i$ (M) | $EC_{50}$ (M) |
|---|---|---|
| Cys$^{4,10}$,DPhe$^7$-α-MSH$_{4-13}$ (APOMSH) | $6.8 \times 10^{-10}$ | $2.6 \times 10^{-11}$ |
| ReMSH | $6.6 \times 10^{-8}$ | $5.4 \times 10^{-10}$ |
| ReCCMSH | $2.9 \times 10^{-9}$ | $3.5 \times 10^{-11}$ |

TABLE 4

Tumor Line: B16-melanoma

| | $^{188}$Re-cc-alphaMSH C57BL/6 1 hr n = 5 | $^{188}$Re-cc-alphaMSH C57BL/6 4 hr n = 7 | $^{188}$Re-cc-alphaMSH C57BL/6 12 hr n = 4 | $^{188}$Re-cc-alphaMSH C57BL/6 24 hr n = 5 |
|---|---|---|---|---|
| Organ (% Dose) | | | | |
| Brain | 0.02 ± 0.01 | 0.01 ± 0.01 | 0.00 ± 0.00 | 0.00 ± 0.01 |
| Blood | 1.60 ± | 0.11 ± | 0.03 ± | 0.01 ± |

TABLE 4-continued

Tumor Line: B16-melanoma

| | 188Re-cc-alphaMSH C57BL/6 1 hr n = 5 | 188Re-cc-alphaMSH C57BL/6 4 hr n = 7 | 188Re-cc-alphaMSH C57BL/6 12 hr n = 4 | 188Re-cc-alphaMSH C57BL/6 24 hr n = 5 |
|---|---|---|---|---|
| | 0.37 | 0.06 | 0.02 | 0.00 |
| Heart | 0.04 ± 0.01 | 0.00 ± 0.00 | 0.00 ± 0.00 | 0.00 ± 0.00 |
| Lung | 0.26 ± 0.04 | 0.01 ± 0.02 | 0.01 ± 0.02 | 0.01 ± 0.01 |
| Liver | 1.07 ± 0.19 | 0.27 ± 0.09 | 0.07 ± 0.02 | 0.06 ± 0.01 |
| Spleen | 0.04 ± 0.03 | 0.00 ± 0.00 | 0.01 ± 0.01 | 0.00 ± 0.00 |
| Stomach | 0.43 ± 0.13 | 0.23 ± 0.15 | 0.02 ± 0.03 | 0.01 ± 0.01 |
| Intestines | 5.07 ± 1.83 | 4.37 ± 1.29 | 0.15 ± 0.09 | 0.17 ± 0.14 |
| Large Intestine | 0.20 ± 0.06 | 3.67 ± 0.99 | 0.09 ± 0.06 | 0.09 ± 0.03 |
| Small Intestine | 4.86 ± 1.82 | 0.69 ± 0.69 | 0.05 ± 0.02 | 0.07 ± 0.15 |
| Kidneys | 5.49 ± 0.58 | 2.10 ± 0.56 | 0.38 ± 0.05 | 0.19 ± 0.03 |
| Bladder + Paper | 70.35 ± 4.24 | 86.68 ± 3.27 | 96.99 ± 1.69 | 98.09 ± 0.78 |
| Bladder | 54.86 ± 30.57 | 29.07 ± 37.27 | 0.44 ± 0.61 | 0.24 ± 0.29 |
| age Paper | 15.49 ± 32.30 | 57.61 ± 39.94 | 96.54 ± 2.20 | 97.84 ± 1.07 |
| Muscle | 0.03 ± 0.02 | 0.00 ± 0.00 | 0.00 ± 0.00 | 0.00 ± 0.00 |
| Pancreas | 0.09 ± 0.02 | 0.00 ± 0.01 | 0.00 ± 0.00 | 0.01 ± 0.01 |
| Tumor | 4.63 ± 1.34 | 3.69 ± 2.25 | 1.55 ± 1.17 | 0.98 ± 0.68 |
| rcass | 12.08 ± 2.82 | 2.56 ± 0.50 | 0.76 ± 0.36 | 0.42 ± 0.13 |
| Organ (% D/GM) | | | | |
| Brain | 0.05 ± 0.03 | 0.03 ± 0.04 | 0.01 ± 0.02 | 0.01 ± 0.02 |
| Blood | 1.34 ± 0.32 | 0.09 ± 0.05 | 0.02 ± 0.01 | 0.00 ± 0.00 |
| Heart | 0.55 ± 0.18 | 0.01 ± 0.02 | 0.06 ± 0.08 | 0.02 ± 0.04 |
| Lung | 1.83 ± 0.44 | 0.13 ± 0.15 | 0.10 ± 0.13 | 0.14 ± 0.14 |
| Liver | 1.26 ± 0.16 | 0.26 ± 0.08 | 0.06 ± 0.01 | 0.05 ± 0.01 |
| Spleen | 0.78 ± 0.55 | 0.12 ± 0.14 | 0.15 ± 0.18 | 0.04 ± 0.05 |
| Stomach | 2.91 ± 1.33 | 1.07 ± 0.70 | 0.08 ± 0.08 | 0.06 ± 0.05 |
| Intestines | 3.48 ± 1.20 | 2.51 ± 1.03 | 0.07 ± 0.04 | 0.09 ± 0.07 |
| Large Intestine | 0.43 ± 0.16 | 6.54 ± 2.20 | 0.14 ± 0.10 | 0.13 ± 0.05 |
| Small Intestine | 5.02 ± 1.90 | 0.61 ± 0.72 | 0.03 ± 0.01 | 0.07 ± 0.14 |
| Kidneys | 22.16 ± 1.84 | 8.23 ± 2.59 | 1.36 ± 0.18 | 0.75 ± 0.20 |
| | 0.44 ± 0.25 | 0.04 ± 0.08 | 0.02 ± 0.00 | 0.02 ± 0.02 |
| Pancreas | 0.41 ± 0.05 | 0.04 ± 0.06 | 0.00 ± 0.00 | 0.05 ± 0.08 |
| | 10.89 ± 2.27 | 6.21 ± 1.63 | 3.24 ± 0.63 | 1.72 ± 0.39 |
| /Blood | 8.09 | 68.77 | 120.98 | 207.90 |
| /Muscle | 24.42 | 136.92 | 149.71 | 76.97 |

TABLE 5

Tumor Line: B16-melanoma

| | 99mTc-cc-alphaMSH C57BL/6 30 min n = 5 | 99mTc-cc-alphaMSH C57BL/6 1 hr n = 5 | 99mTc-cc-alphaMSH C57BL/6 4 hr n = 5 | 99mTc-cc-alphaMSH C57BL/6 24 hr n = 6 |
|---|---|---|---|---|
| Organ (% Dose) | | | | |
| Brain | 0.06 ± 0.01 | 0.02 ± 0.01 | 0.01 ± 0.01 | 0.00 ± 0.00 |
| Blood | 3.67 ± 0.33 | 1.76 ± 0.13 | 0.65 ± 0.21 | 0.07 ± 0.04 |
| Heart | 0.10 ± 0.01 | 0.04 ± 0.01 | 0.02 ± 0.01 | 0.01 ± 0.01 |
| Lung | 0.42 ± 0.03 | 0.18 ± 0.02 | 0.06 ± 0.01 | 0.01 ± 0.00 |
| Liver | 1.82 ± 0.24 | 1.12 ± 0.29 | 0.55 ± 0.09 | 0.06 ± 0.01 |
| Spleen | 0.06 ± 0.02 | 0.02 ± 0.01 | 0.02 ± 0.00 | 0.00 ± 0.00 |
| Stomach | 0.57 ± 0.19 | 0.47 ± 0.10 | 0.37 ± 0.20 | 0.00 ± 0.00 |
| Intestines | 3.37 ± 0.33 | 4.53 ± 0.75 | 6.03 ± 1.79 | 0.15 ± 0.07 |
| Large Intestine | 0.40 ± 0.02 | 0.39 ± 0.07 | 5.23 ± 1.48 | 0.12 ± 0.05 |
| Small Intestine | 2.96 ± 0.31 | 4.14 ± 0.79 | 0.80 ± 0.36 | 0.03 ± 0.01 |
| Kidneys | 6.33 ± 0.47 | 5.07 ± 0.50 | 3.21 ± 0.57 | 0.32 ± 0.03 |
| Bladder + Paper | 60.52 ± 1.89 | 74.84 ± 2.53 | 81.83 ± 2.45 | 98.49 ± 0.45 |
| Bladder | 57.02 ± 8.21 | 74.41 ± 2.38 | 18.31 ± 33.73 | 0.12 ± 0.15 |
| age Paper | 3.49 ± 7.26 | 0.43 ± 0.40 | 63.51 ± 34.44 | 98.36 ± 0.51 |
| Muscle | 0.06 ± 0.01 | 0.01 ± 0.01 | 0.00 ± 0.00 | 0.00 ± 0.00 |
| Pancreas | 0.15 ± 0.02 | 0.07 ± 0.02 | 0.02 ± 0.02 | 0.00 ± 0.01 |
| Tumor | 3.13 ± 1.54 | 3.49 ± 2.18 | 3.32 ± 1.08 | 0.48 ± 0.27 |
| arcass | 22.94 ± 1.94 | 9.82 ± 0.97 | 4.41 ± 0.61 | 0.41 ± 0.16 |
| Organ (% D/GM) | | | | |
| Brain | 0.18 ± 0.06 | 0.06 ± 0.02 | 0.03 ± 0.03 | 0.01 ± 0.01 |
| Blood | 3.44 ± 0.48 | 1.60 ± 0.09 | 0.62 ± 0.21 | 0.06 ± 0.03 |
| Heart | 1.29 ± 0.25 | 0.53 ± 0.17 | 0.25 ± 0.15 | 0.13 ± 0.13 |
| Lung | 3.50 ± 0.20 | 1.39 ± 0.20 | 0.55 ± 0.12 | 0.10 ± 0.06 |
| Liver | 2.12 ± 0.14 | 2.34 ± 2.19 | 0.65 ± 0.08 | 0.06 ± 0.02 |
| Spleen | 1.07 ± 0.36 | 0.46 ± 0.35 | 0.54 ± 0.19 | 0.18 ± 0.28 |
| Stomach | 4.18 ± 1.11 | 3.18 ± 0.98 | 2.10 ± 0.81 | 0.05 ± 0.04 |
| Intestines | 2.59 ± 0.41 | 3.17 ± 0.74 | 3.76 ± 1.50 | 0.10 ± 0.06 |
| Large Intestine | 0.97 ± 0.11 | 0.82 ± 0.11 | 10.65 ± 4.49 | 0.24 ± 0.17 |
| Small Intestine | 3.36 ± 0.56 | 4.32 ± 1.18 | 0.73 ± 0.41 | 0.03 ± 0.02 |
| Kidneys | 28.05 ± 2.32 | 22.60 ± 2.70 | 14.60 ± 1.88 | 1.22 ± 0.15 |
| Muscle | 0.90 ± 0.10 | 0.17 ± 0.22 | 0.08 ± 0.06 | 0.05 ± 0.05 |
| Pancreas | 0.82 ± 0.16 | 0.35 ± 0.08 | 0.14 ± 0.14 | 0.04 ± 0.05 |
| Tumor | 10.74 ± 1.61 | 10.88 ± 0.54 | 9.51 ± 1.97 | 1.38 ± 0.36 |
| Tumor/Blood | 3.12 | 6.80 | 15.24 | 22.10 |
| Tumor/Muscle | 11.82 | 63.37 | 108.80 | 23.73 |

REFERENCES

Bagutti, C., Stolz, B., Albert, R., Bruns, C., Pless, J., Eberle, A. N. (1994) *Int. J. Cancer* 58, 749–755.

Bakker, W. H., Albert, R., Bruns, C., Breeman, W. A. P., Hofland, L. J., Marbach, P., Pless, J., Pralet, D., Stoltz, B., Koper, J. W., Lamberts, S. W. J., Visser, T. J., Krenning, E. P. (1991) *Life Sci.* 49, 1583–1591.

Bard, D. R., Knight, C. G., Page-Thomas, D. P. (1990) *Br. J. Cancer* 62, 919–922.

Betz et al., 1994, Basic Neurochem. Molecular Cell, (Raven Press Ltd, New York) 5th Ed., 681–699

Bickel, et al., 1993, "Pharmacologic effects in vivo in brain by vector-mediated peptide drug delivery" Proc. Natl. Acad. Sci. USA 90(7)2618–2622

Brem et al., "Polymers as controlled drug delivery devised for the treatment of malignant brain tumors" *Eur. J. Pharm. Biopharm* 39:2–7 (1993)

Bryan, J. C., Stenkamp, R. E., Tulip, T. H., Mayer, J. M. (1987) *Inorg. Chem.* 26, 2283–2288.

Chi, D. Y., O'Neil, J. P., Anderson, C. J., Welch, M. J., Katzenellenbogen, J. A. (1994) *J. Med. Chem.* 37, 928–937.

Cody, W. L., Mahoney, M., Knittel, J. J., Hruby, V. J., Castrucci, A. M. de L., Hadley, M. E. (1985) *J. Med. Chem.* 28, 583–588.

Ellman, G. L. (1959) *Arch. Biochem. Biophys.* 82, 70–77.

Franco, R., Moura, J. J. G., Moura, I. (1995) *J. Biol. Chem.* 270, 26352–26357.

Fritzberg, A. R., Abrams, P. G., Beaumier, P. L., Kasina, S., Morgan, A. C., Rao, T. N., Reno, J. M., Sanderson, J. A., Srinivasan, A., Wilbur, D. S., Vanderheyden, J. L. (1988) *Proc. Natl. Acad. Sci. U. S. A.* 85, 4025–4029.

Garg, P. K., Alston, K. L., Welsh, P.C., Zalutsky, M. R. (1996) Bioconjugate Chem. 7, 233–239.

Giblin, M. F., Jurisson, S. S., and Quinn, T. P. (1997) *Bioconjugate Chem.* 8, 347–353.

Grove, D. E., Wilkinson, G. (1966) *J. Chem. Soc. A* 1224–1230.

Grummon, G., Rajagopalan, R., Palenik, G. J., Koziol, A. E., Nosco, D. L. (1995) *Inorg. Chem.* 34, 1764–1772.

Hansen, L., Cini, R., Taylor, A., Marzilli, L. G. (1992) *Inorg. Chem.* 31, 2801–2808.

Hruby, V. J., Sharma, S. D., Toth, K., Jaw, J. Y., Al-Krenning, E. P., Bakker, W. H., Kooij, P. P. M., Breeman, W. A. P., Oei, H. Y., deJong, M., Reubi, J. C., Visser, T. J., Bruns, C., Kwekkeboom, D. J., Reijs, A. E. M., vanHagen, P. M., Koper, J. W., Lamberts, S. W. J. (1992) *J. Nucl. Med.* 33, 652–658.

Iverson, B. L., Iverson, S. A., Roberts, V. A., Getzoff, E. D., Tainer, J. A., Benkovic, S. J. Lerner, R. A. (1990) *Science* 249, 659–662.

Kellis, J. T. Jr., Todd, R. J., Arnold, F. H. (1991) *BioTechnology* 9, 994–995.

Klemba, M., Gardner, K. H., Marino, S., Clarke, N. D., Regan, L. (1995) Nature Structural Biology 2, 368–373.

Kruck, T. P. A., Lau, S., Sarkar, B. (1976) *Can. J. Chem.* 54, 1300–1308.

Lau, S., Laussac, J. P., Sarkar, B. (1989) *Biochem. J.* 257, 745–750.

Lever, S. Z., Baidoo, K. E., Mahmood, A. (1990) *Inorg. Chim. Acta* 176, 183–184.

Liu, S., Edwards, D. S., Looby, R. J., Harris, A. R., Poirier, M. J., Barrett, J. A., Heminway, S. J., Carroll, T. R. (1996) *Bioconjugate Chem.* 7, 63–71.

Obidi, F., Sawyer, T. K., Hadley, M. E., (1993) *Ann. N. Y. Acad. Sci.* 680, 51–63.

Pardridge, et al., 1992, "Blood-brain barrier and new approaches to brain drug delivery" West J. Med. 156(3) 281–286 Pardridge, 1992, "Recent Developments in peptide drug delivery to the brain" Pharm. Toxicol. 71(1) :3–10

Piotto, M., Saudek, V., Sklenar, V. (1992) *J. Biomol. NMR* 2, 661–665.

Powell, M. J. D. (1977) *Mathematical Programming* 12, 241–254.

Rao, T. N., Adhikesavalu, D., Camerman, A., Fritzberg, A. R. (1991) *Inorg. Chem.* 180, 63–67.

Regan, L. (1993) *A. Rev. Biophys. Biomol. Struct.* 22, 257–281.

Sahm, U. G., Olivier, G. W. J., Branch, S. K., Moss, S. H., Pouton, C. W. (1994) *Peptides* 15, 441–446.

Sawyer, T. K., Sanfilippo, P. J., Hruby, V. J., Engel, M. H., Heward, C. B., Burnett, J. B., Hadley, M. E. (1980) *Proc. Natl. Acad. Sci. USA* 77, 5754–5758.

Siegrist, W. and Eberle, A. N. (1986) *Anal. Biochem.* 159, 191–197.

Siegrist, W., Oestreicher, M., Stutz, S., Girard, J., and Eberle, A. N. (1988) J. Recept. Res. 8, 323–343.

Siegrist, W., Solca, F., Stutz, S., Giuffre, L., Carrel, S., Girard, J., Eberle, A. N. (1989) *Cancer Res.* 49, 6352–6358.

Tatro, J. B., Entwistle, M. L., Lester, B. R., Reichlin, S. (1989) *Cancer Res.* 50, 1237–1242.

Vaidyanathan, G. and Zalutsky, M. R. (1997) *Nucl. Med. Biol.* 24, 171–178.

Vanbilloen, H. P., Bormans, G. M., DeRoo, M. J., Verbruggen, A. M. (1995) *Nucl. Med. Biol.* 22, 325–338.

Varnum, J. M., Thakur, M. L., Schally, A. V., Jansen, S. A., Mayo, K. H. (1994) *J. Biol. Chem.* 209, 12583–12588.

Varnum, J. M., Thakur, M., Mayo, K. H., Jansen, S. A. (1996) *J. Phys. Chem.* 100, 14630–14636.

Wraight, E. P., Bard, D. R., Maughan, T. S., Knight, C. G., Page-Thomas, D. P. (1992) *Br. J. Radiol.* 65, 112–118.

What is claimed is:

1. A compound for use as a diagnostic or therapeutic pharmaceutical, said compound consisting essentially of:

an alpha-melanotropin stimulating hormone; and a radionuclide directly bound in said alpha-melanotropin stimulating hormone analog includes a disulfide bond and an oxo group; said disulfide bond being replaced by a radionuclide; said radionuclide being a transition element; said radionuclide being bound to the two sulfide groups of said disulfide bond and said oxo groups; and said radionuclide being bound to two other groups selected from the group comprising amide, amine or sulfhydryl.

2. The compound of claim 1, wherein said alpha-melanotropin stimulating hormone is cyclic.

* * * * *

SEQUENCE LISTING

<160> NUMBER OF SEQ ID NOS: 3

<210> SEQ ID NO 1
<211> LENGTH: 13
<212> TYPE: PRT
<213> ORGANISM: Unknown
<220> FEATURE:
<223> OTHER INFORMATION: Description of Unknown Organism: mouse, human or synthetic

<400> SEQUENCE: 1

```
Ser Tyr Ser Met Glu His Phe Arg Trp Gly Lys Pro Val
  1               5                  10

<210> SEQ ID NO 2
<211> LENGTH: 4
<212> TYPE: PRT
<213> ORGANISM: Unknown
<220> FEATURE:
<223> OTHER INFORMATION: Description of Unknown Organism:mouse, human or
      synthetic

<400> SEQUENCE: 2

His Phe Arg Trp
  1

<210> SEQ ID NO 3
<211> LENGTH: 4
<212> TYPE: PRT
<213> ORGANISM: Unknown
<220> FEATURE:
<223> OTHER INFORMATION: Description of Unknown Organism:mouse, human or
      synthetic

<400> SEQUENCE: 3

Cys Gly Cys Gly
```